United States Patent
Yamamoto et al.

(10) Patent No.: US 12,329,359 B2
(45) Date of Patent: Jun. 17, 2025

(54) RIGID SCOPE DEVICE

(71) Applicants: NATIONAL UNIVERSITY CORPORATION HAMAMATSU UNIVERSITY SCHOOL OF MEDICINE, Shizuoka (JP); HAMAMATSU MEDICAL SOLUTIONS CORP., Shizuoka (JP)

(72) Inventors: Seiji Yamamoto, Hamamatsu (JP); Masaki Orimoto, Hamamatsu (JP)

(73) Assignees: NATIONAL UNIVERSITY CORPORATION HAMAMATSU UNIVERSITY SCHOOL OF MEDICINE, Shizuoka (JP); HAMAMATSU MEDICAL SOLUTIONS CORP., Shizuoka (JP)

( * ) Notice: Subject to any disclaimer, the term of this patent is extended or adjusted under 35 U.S.C. 154(b) by 404 days.

(21) Appl. No.: 17/788,942

(22) PCT Filed: Dec. 15, 2020

(86) PCT No.: PCT/JP2020/046814
§ 371 (c)(1),
(2) Date: Jun. 24, 2022

(87) PCT Pub. No.: WO2021/131921
PCT Pub. Date: Jul. 1, 2021

(65) Prior Publication Data
US 2023/0029750 A1  Feb. 2, 2023

(30) Foreign Application Priority Data
Dec. 27, 2019  (JP) .................................. 2019-239514

(51) Int. Cl.
*A61B 1/00* (2006.01)

(52) U.S. Cl.
CPC ........ *A61B 1/00193* (2013.01); *A61B 1/0005* (2013.01); *A61B 1/00096* (2013.01); *A61B 1/00183* (2013.01); *A61B 1/00188* (2013.01)

(58) Field of Classification Search
CPC .............. A61B 1/0005; A61B 1/00052; A61B 1/00188; A61B 1/00193; A61B 1/00194;
(Continued)

(56) References Cited

U.S. PATENT DOCUMENTS

| | | |
|---|---|---|
| 4,873,572 A | 10/1989 | Miyazaki et al. |
| 5,588,948 A | 12/1996 | Takahashi et al. |

(Continued)

FOREIGN PATENT DOCUMENTS

| | | |
|---|---|---|
| JP | S63244011 A | 10/1988 |
| JP | H0654803 A * | 3/1994 |

(Continued)

OTHER PUBLICATIONS

International Search Report and Written Opinion in International Application No. PCT/JP2020/046814 dated Mar. 9, 2021, 11 pages.

(Continued)

*Primary Examiner* — Michael J Carey
*Assistant Examiner* — Stephen Floyd London
(74) *Attorney, Agent, or Firm* — Marshall, Gerstein & Borun LLP

(57) ABSTRACT

A single solid-state image sensing device is disposed for a first optical system and a second optical system provided in a rigid endoscope. The first image formed by the first light beam emerging from the observation target and passing through the first optical system and the second image formed by the second light beam emerging from the observation target and passing through the second optical system are formed on the imaging surface of the solid-state image sensing device. The solid-state image sensing device then (Continued)

converts the first image and the second image into electric signals. In the picture display unit, the first picture corresponding to the first image and the second picture corresponding to the second image are displayed on the display surface based on the electric signal obtained by the solid-state image sensing device.

3 Claims, 12 Drawing Sheets

(58) Field of Classification Search
CPC .......................... A61B 1/00197; A61B 1/042; G02B 23/2415; G02B 23/2438
See application file for complete search history.

(56) References Cited

U.S. PATENT DOCUMENTS

| | | | |
|---|---|---|---|
| 5,720,706 A | 2/1998 | Takahashi et al. | |
| 6,139,490 A * | 10/2000 | Breidenthal | H04N 13/296 |
| | | | 348/E13.016 |
| 6,191,809 B1 * | 2/2001 | Hori | H04N 13/122 |
| | | | 348/E13.016 |
| 2005/0001899 A1 * | 1/2005 | Banju | A61B 1/00048 |
| | | | 348/E13.041 |
| 2009/0292170 A1 * | 11/2009 | Boebel | G02B 23/2415 |
| | | | 600/111 |
| 2012/0277527 A1 * | 11/2012 | Sood | A61B 1/0005 |
| | | | 600/109 |
| 2016/0070094 A1 | 3/2016 | Togino | |
| 2016/0120393 A1 * | 5/2016 | Helmsworth | A61B 1/00193 |
| | | | 600/103 |
| 2016/0120397 A1 | 5/2016 | Namii et al. | |
| 2016/0205387 A1 * | 7/2016 | Kasumi | G09G 5/00 |
| | | | 348/53 |
| 2016/0295194 A1 * | 10/2016 | Wang | A61B 1/00057 |
| 2017/0258297 A1 * | 9/2017 | Suga | G03B 15/14 |
| 2018/0042453 A1 * | 2/2018 | Hino | G02B 23/2415 |
| 2018/0263474 A1 * | 9/2018 | Imade | A61B 1/045 |
| 2018/0270453 A1 | 9/2018 | Kupferschmid et al. | |
| 2019/0021578 A1 | 1/2019 | Hu et al. | |
| 2019/0053700 A1 * | 2/2019 | Tesar | G02B 21/368 |
| 2020/0268236 A1 * | 8/2020 | Chiba | A61B 1/00194 |

FOREIGN PATENT DOCUMENTS

| | | | | |
|---|---|---|---|---|
| JP | H11168717 A | | 6/1999 | |
| JP | 2001-078229 A | | 3/2001 | |
| WO | WO-2010079817 A1 * | | 7/2010 | ......... A61B 1/00188 |
| WO | WO-2014/147856 A1 | | 9/2014 | |
| WO | WO-2015/016166 A1 | | 2/2015 | |
| WO | WO-2015/072427 A1 | | 5/2015 | |

OTHER PUBLICATIONS

International Preliminary Report on Patentability in International Application No. PCT/JP2020/046814 dated Dec. 14, 2021, 18 pages.

* cited by examiner

RIGID SCOPE DEVICE

TECHNICAL FIELD

The present disclosure relates to a rigid scope device.

BACKGROUND ART

Japanese Patent Application Laid-Open (JP-A) No. 11-168717 describes an invention related to a videoscope. In this videoscope, a left-eye objective lens and a right-eye objective lens are provided in the lens barrel of an endoscope, and an observation target video captured by these objective lenses is converted into a video signal by an image sensing device. The video signal is then input to a stereoscopic picture signal processing unit. The stereoscopic picture signal processing unit generates a stereoscopic picture of the observation target on the basis of the video signal.

SUMMARY OF INVENTION

Technical Problem

However, in the prior art according to Patent Literature 1, an image sensing device is provided for each of the left-eye objective lens and the right-eye objective lens, and a stereoscopic picture generated by processing signals from these image sensing devices is displayed on a picture display unit. Accordingly, depending on the signal processing, it is conceivable that the stereoscopic picture of the observation target displayed on the picture display unit and the actual state of the observation target deviate from each other.

In consideration of the above fact, an object of the present disclosure is to provide a rigid scope device that allows the observation of an observation target in a state closer to an actual state.

Solution to Problem

A rigid scope device according to the first aspect includes an outer lens barrel made of a rigid material and extending in a first direction, a first inner lens barrel made of a rigid material, disposed in the outer lens barrel, and extending in the first direction, a first optical system disposed in the first inner lens barrel and including a first optical axis extending in the first direction, a second inner lens barrel made of a rigid material, disposed adjacent to the first inner lens barrel in the outer lens barrel, and extending in parallel with the first inner lens barrel, a second optical system disposed in the second inner lens barrel and including a second optical axis extending in parallel with the first optical axis, a single solid-state image sensing device that is disposed on one side of the first optical system and the second optical system in the first direction, that includes an imaging surface on which a first image is formed by a first light beam emerging from an observation target and passing through the first optical system, and a second image is formed by a second light beam emerging from the observation target and passing through the second optical system, and that is configured to convert light received by the imaging surface into an electric signal, and a picture display unit including a display surface configured to display a first picture corresponding to the first image and a second picture corresponding to the second image based on the electric signal.

The rigid scope device according to the first aspect includes the outer lens barrel made of a rigid material and extending in the first direction, and the first inner lens barrel and the second inner lens barrel are disposed in the outer lens barrel. The first inner lens barrel and the second inner lens barrel are each made of a rigid material, the first inner lens barrel extends in the first direction, and the second inner lens barrel is disposed adjacent to the first inner lens barrel and extends in parallel with the first inner lens barrel.

The first optical system including the first optical axis extending in the first direction is disposed inside the first inner lens barrel, and the second optical system including the second optical axis extending in parallel with the first optical axis is disposed inside the second inner lens barrel. The solid-state image sensing device is disposed on one side of the first optical system and the second optical system in the first direction. Accordingly, the observation target can be stereoscopically viewed using the images formed on the imaging surface of the solid-state image sensing device by the first optical system and the second optical system.

Meanwhile, in a configuration in which the solid-state image sensing device is provided for each of the first optical system and the second optical system, a stereoscopic picture of the observation target is generated by processing signals based on images formed on different imaging surfaces. Therefore, depending on the signal processing, the stereoscopic picture of the observation target obtained based on these images may deviate from the actual state of the observation target.

In this case, in the embodiment, the single solid-state image sensing device is disposed for the first optical system and the second optical system. The first image formed by the first light beam emerging from the observation target and passing through the first optical system and the second image formed by the second light beam emerging from the observation target and passing through the second optical system are formed on the imaging surface of the solid-state image sensing device. The solid-state image sensing device then converts the first image and the second image into electric signals.

On the other hand, in the picture display unit, the first picture corresponding to the first image and the second picture corresponding to the second image are displayed on the display surface based on the electric signal obtained by the solid-state image sensing device. Accordingly, in this aspect, when the observer views the display surface of the picture display unit, the observer can perform stereoscopic viewing of the observation target by the parallel method by using the first image and the second image obtained by performing signal processing on the first picture and the second picture in a similar manner.

The rigid scope device according to the second aspect, in the rigid scope device according to the first aspect, further includes an optical path adjustment unit interposed between the outer lens barrel and the solid-state image sensing device. The optical path adjustment unit is configured to adjust at least one of the first light beam or the second light beam on the display surface such that the first picture and the second picture do not overlap each other and a reference point of the observation target in the first picture and the reference point in the second picture are located at a same height as viewed by an observer.

In the rigid scope device according to the second aspect, the optical path adjustment unit is interposed between the outer lens barrel and the solid-state image sensing device. The optical path adjustment unit adjusts at least one of the first light beam that has passed through the first optical system or the second light beam that has passed through the second optical system. As a result, on the display surface of the picture display unit, the first picture and the second picture are displayed so that the reference point of the observation target in the first picture and the reference point in the second picture have the same height as viewed from the observer without overlapping each other.

In the rigid scope device according to the third aspect, the optical path adjustment unit is configured to adjust the first light beam and the second light beam and includes a first lens prism disposed on one side of the first optical system in the first direction and configured to refract the first light beam to one side in a second direction at an opposite side of the first optical system from the second optical system, the second direction being a detection along a straight line passing through the first optical axis and the second optical axis as viewed from the first direction, a first position adjustment lens system that adjusts the first light beam refracted by the first lens prism such that the first image is formed at a predetermined position, a first focus adjustment lens system that is disposed on one side of the first position adjustment lens system in the first direction and adjusts a focal position of the first optical system, a second lens prism configured to refract the first light beam passing through the first focus adjustment lens system to the other side in the second direction, a third lens prism disposed on one side of the second optical system in the first direction and configured to refract the second light beam toward the other side in the second direction, a second position adjustment lens system that adjusts the second light beam refracted by the third lens prism such that the second image is formed at a predetermined position, a second focus adjustment lens system that is disposed on one side of the second position adjustment lens system in the first direction and adjusts a focal position of the second optical system, and a fourth lens prism configured to refract the second light beam passing through the second focus adjustment lens system to the one side in the second direction, in the rigid scope device according to the second aspect.

In the rigid scope device according to the third aspect, the optical path adjustment unit adjusts the first light beam that has passed through the first optical system and the second light beam that has passed through the second optical system. More specifically, the optical path adjustment unit includes the first lens prism, the first position adjustment lens system, the first focus adjustment lens system, and the second lens prism through which the first light beam passes and also includes the third lens prism, the second position adjustment lens system, the second focus adjustment lens system, and the fourth lens prism through which the second light beam passes.

The first lens prism is disposed on one side of the first optical system in the first direction, and the first light beam passing through the first optical system is refracted by the first lens prism and travels to the first position adjustment lens system. The first light beam is adjusted by the first position adjustment lens system such that the first image is formed at a predetermined position on the imaging surface.

The first light beam having passed through the first position adjustment lens system travels to the first focus adjustment lens system disposed on one side of the first position adjustment lens system which is located in the first direction. The focal position of the first optical system is adjusted such that the first light beam converges at a predetermined point through the first focus adjustment lens system. The first light beam that has passed through the first focus adjustment lens system travels to the imaging surface through the second lens prism.

The third lens prism is disposed on one side of the second optical system in the first direction, and the second light beam passing through the second optical system is refracted by the third lens prism and travels to the second position adjustment lens system. The second light beam is adjusted by the second position adjustment lens system such that the second image is formed at a predetermined position on the imaging surface.

The second light beam having passed through the second position adjustment lens system travels to the second focus adjustment lens system disposed on one side of the second position adjustment lens system which is located in the first direction. The focal position of the second optical system is adjusted such that the second light beam converges at a predetermined point through the second focus adjustment lens system. The second light beam that has passed through the second focus adjustment lens system travels to the imaging surface through the fourth lens prism.

In the configuration in which the first light beam linearly advances from the first optical system toward the first position adjustment lens system along the first direction, it is conceivable that a space for arranging the first position adjustment lens system and the first focus adjustment lens system cannot be secured. On the other hand, in the configuration in which the first light beam linearly advances from the first focus adjustment lens system toward the solid-state image sensing device along the first direction, it is conceivable that the degree of freedom of the shape and size of the solid-state image sensing device is reduced.

In the configuration in which the second light beam linearly advances from the second optical system toward the second position adjustment lens system along the first direction, it is conceivable that a space for arranging the second position adjustment lens system and the second focus adjustment lens system cannot be secured. On the other hand, in the configuration in which the second light beam linearly advances from the second focus adjustment lens system toward the solid-state image sensing device along the first direction, it is conceivable that the degree of freedom of the shape and size of the solid-state image sensing device is reduced.

In this case, in this aspect, in the second direction along the straight line passing through the first optical axis of the first optical system and the second optical axis of the second optical system when viewed from the first direction, the first lens prism refracts the first light beam to one side in the second direction opposite to the second optical system with reference to the first optical system. On the other hand, the second lens prism refracts the first light beam toward the other side in the second direction.

The third lens prism refracts the second light beam toward the other side in the second direction. On the other hand, the fourth lens prism refracts the second light beam toward one side in the second direction.

Therefore, in the aspect, by refracting the first light beam by the first lens prism and refracting the second light beam by the second lens prism, it is possible to secure a space for arranging the first position adjustment lens system, the first focus adjustment lens system, the second position adjustment lens system, and the second focus adjustment lens system. Furthermore, by refracting the first light beam by the second lens prism and refracting the second light beam by the fourth lens prism, the distance between the optical paths of the first light beam and the second light beam can be adjusted in accordance with the shape and size of the solid-state image sensing device.

In the rigid scope device according to the fourth aspect, the optical path adjustment unit further includes a first shielding portion that is disposed on the one side in the second direction between the first position adjustment lens system and the first focus adjustment lens system and shields the first light beam such that a picture corresponding to a portion included in the first image and not included in the second image is not included in the first picture, and a second shielding portion that is disposed on the other side in the second direction between the second position adjustment lens system and the second focus adjustment lens system and shields the second light beam such that a picture corresponding to a portion included in the second image and not included in the first image is not included in the second picture, in the rigid scope device according to the third aspect.

In the rigid scope device according to the fourth aspect, the optical path adjustment unit includes the first shielding portion and the second shielding portion. The first shielding portion is disposed on one side in the second direction between the first position adjustment lens system and the first focus adjustment lens system, and the first light beam is shielded by the first shielding portion such that a picture corresponding to a portion included in the first image and not included in the second image is not included in the first picture.

On the other hand, the second shielding portion is disposed on the other side in the second direction between the second position adjustment lens system and the second focus adjustment lens system, and the second light beam is shielded by the second shielding portion such that a picture corresponding to a portion included in the second image and not included in the first image is not included in the second picture. Accordingly, in the aspect, since the same part of the observation target can be displayed in the first picture and the second picture displayed on the display surface of the picture display unit, the observer can observe the observation target by stereoscopic vision with high accuracy.

The rigid scope device according to the fifth aspect, in the rigid scope device according to the any one of the first to fourth aspects, further includes a picture visibility assist unit that is movable in a direction orthogonal to the display surface and includes a first magnifying lens for a left eye configured to enlarge the first picture and a second magnifying lens for a right eye configured to enlarge the second picture.

In the rigid scope device according to the fifth aspect, the picture visibility assist unit movable in a direction orthogonal to the display surface of the picture display unit is provided. The picture visibility assist unit includes the first magnifying lens for the left eye and the second magnifying lens for the right eye. By moving the picture visibility assist unit in the direction orthogonal to the display surface, the first picture can be enlarged by the first magnifying lens, and the second picture can be enlarged by the second magnifying lens. Therefore, according to this aspect, the observer can observe the observation target in more detail.

In rigid scope device according to the sixth aspect, in the rigid scope device according to the fifth aspect, the picture visibility assist unit further includes a picture separation unit configured to hide the second picture when viewed from the first magnifying lens and hide the first picture when viewed from the second magnifying lens.

In the rigid scope apparatus according to the sixth aspect, the picture visibility assist unit includes the picture separation unit, and when the observer views the display surface of the picture display unit with the right eye from the first magnifying lens, the first picture is visible, but the second picture is hidden by the picture separation unit. When the observer looks at the display surface of the picture display unit with the left eye from the second magnifying lens, the second picture is visible, but the first picture is hidden by the picture separation unit. Therefore, in the aspect, the observer can observe the observation target by more accurate stereoscopic vision.

Advantageous Effects of Invention

As described above, the rigid scope device according to the present disclosure has an excellent effect of allowing the observation of an observation target in a state closer to an actual state.

DESCRIPTION OF EMBODIMENTS

Figure 1:
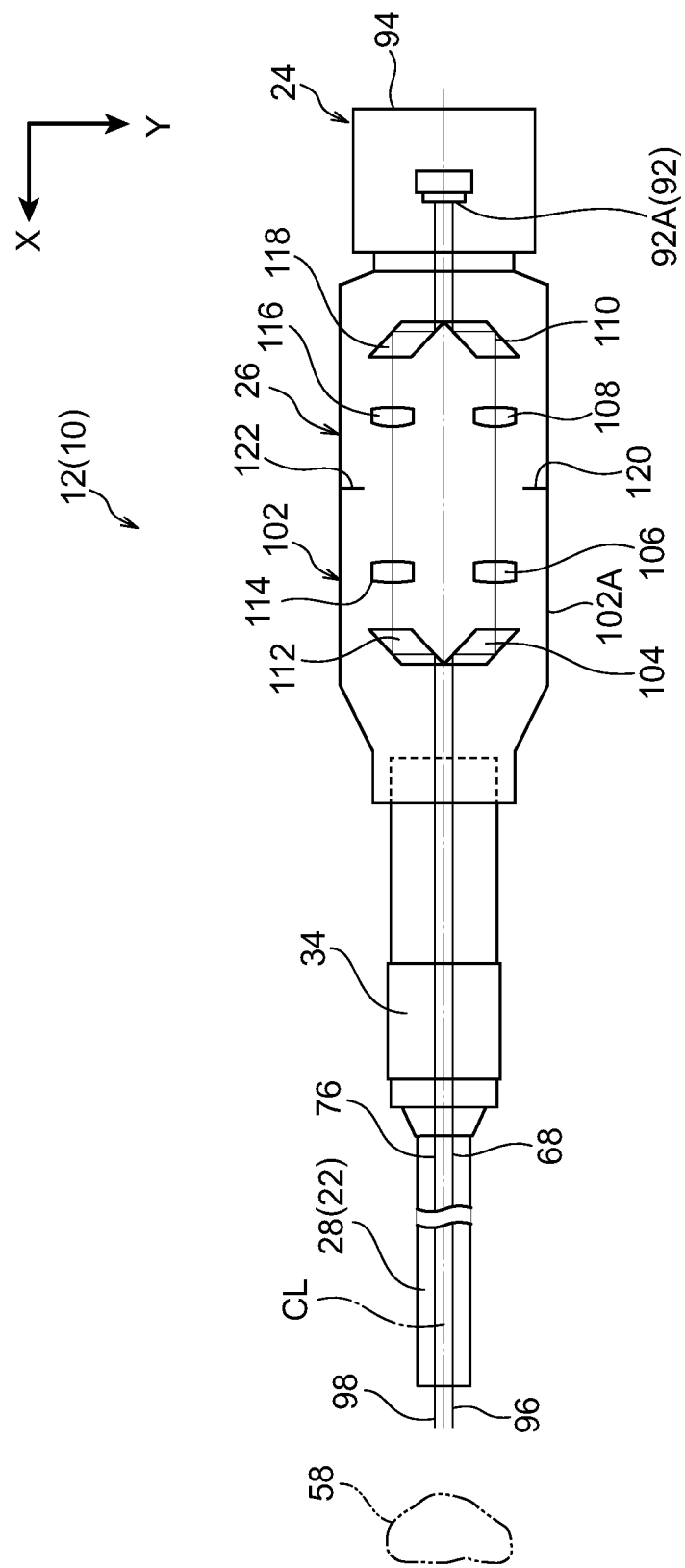
FIG. 1 is a schematic configuration diagram schematically illustrating the configuration of a rigid endoscope according to the present embodiment.

An example of an embodiment of a rigid scope device according to the present disclosure will be described below with reference to FIGS. 1 to 12. As illustrated in FIG. 7, a rigid scope device 10 according to the present embodiment includes a rigid endoscope 12, a first support arm 14 that supports the rigid endoscope 12, a picture display device 16, and a second support arm 18 that supports the picture display device 16.

Figure 6:
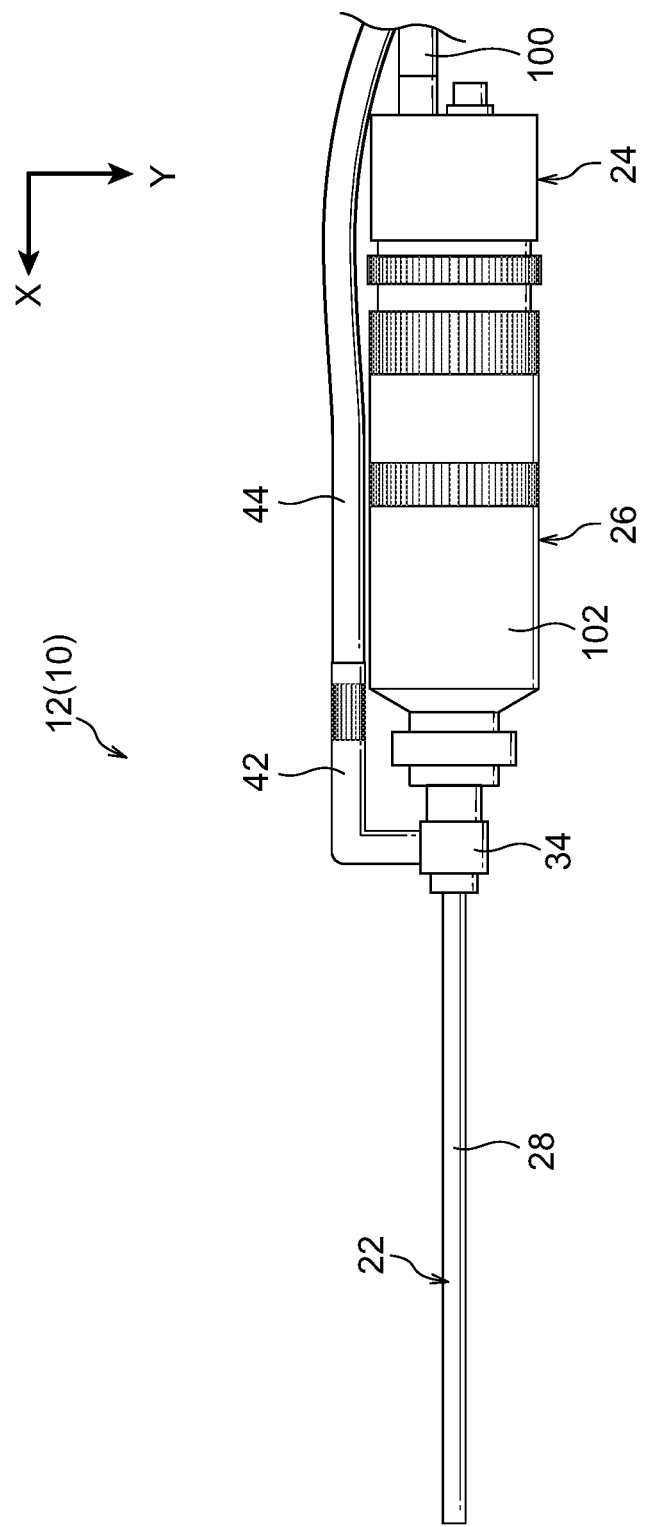
FIG. 6 is an external view schematically illustrating the configuration of the rigid endoscope according to the embodiment.
Figure 7:
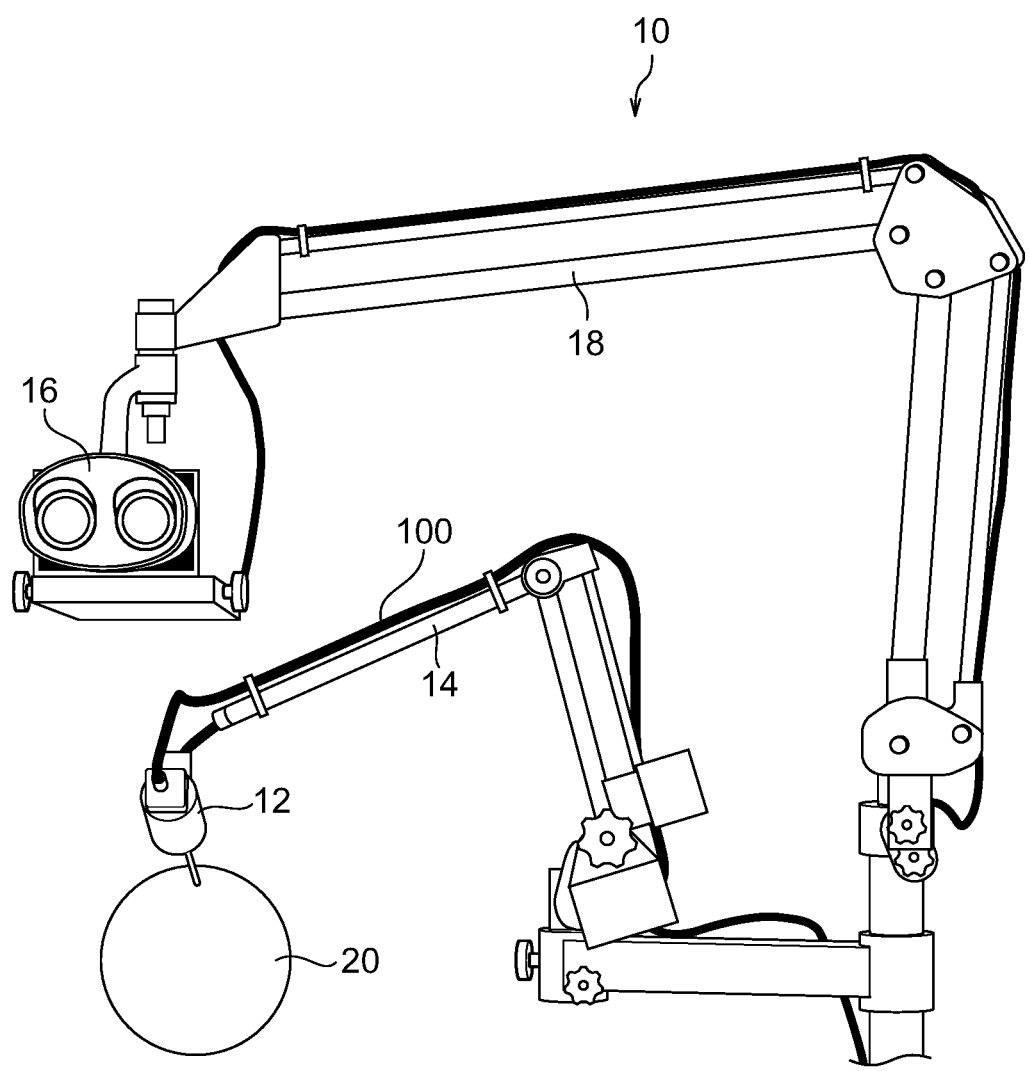
FIG. 7 is an external view schematically illustrating the configuration of the rigid scope device according to the embodiment.

As illustrated in FIG. 6, the rigid endoscope 12 includes an insertion portion 22 that can be inserted into a subject 20 (see FIG. 9), an imaging device 24, and an attachment portion 26 as an optical path adjustment unit interposed between the insertion portion 22 and the imaging device 24.

Figure 2:
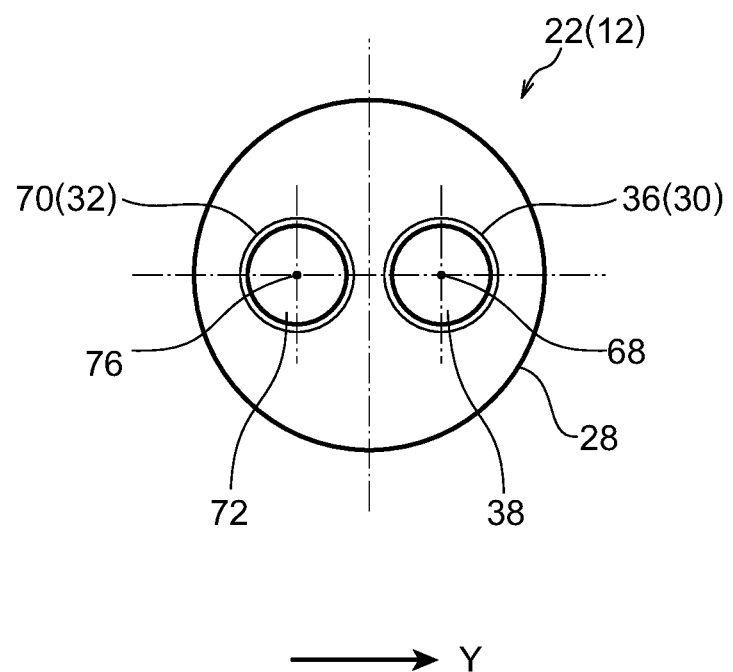
FIG. 2 is a front view schematically illustrating the configuration of a distal end portion of the rigid endoscope according to the embodiment.
Figure 4:
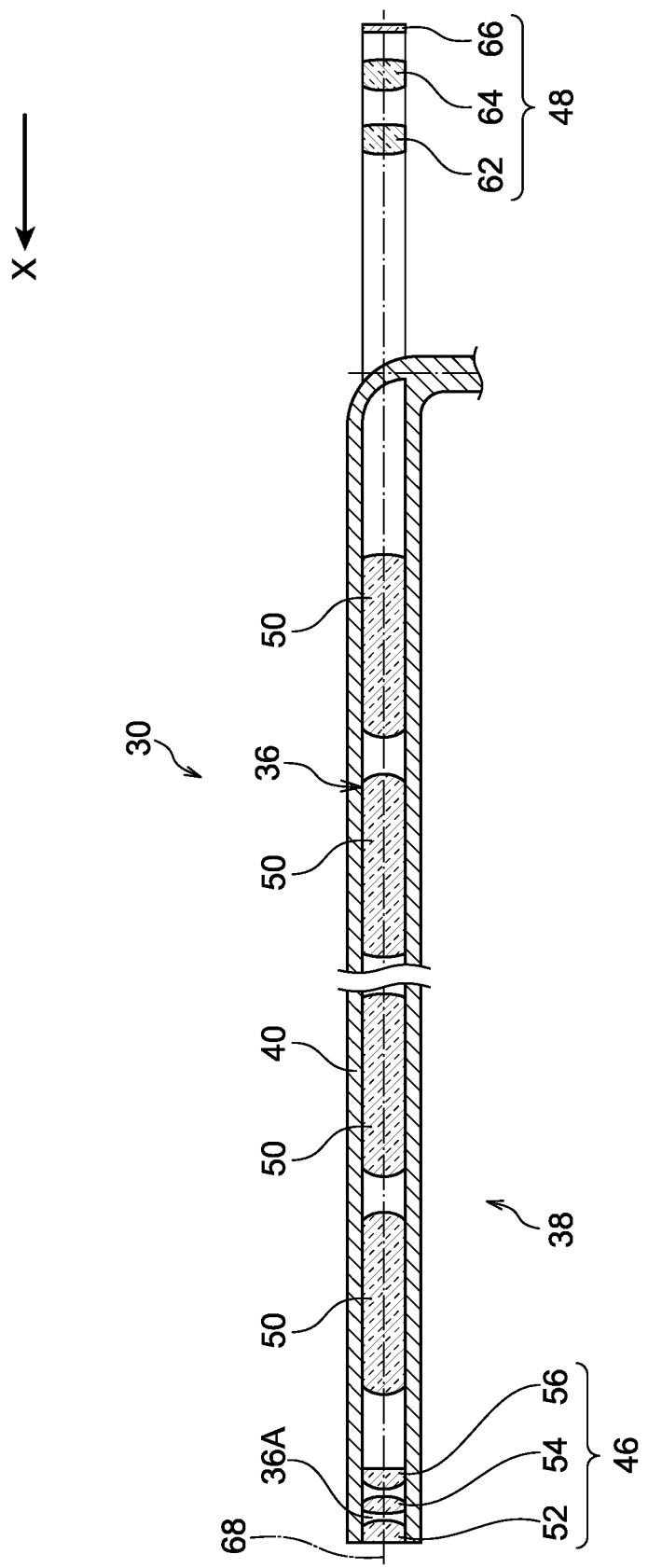
FIG. 4 is a cross-sectional view schematically illustrating the configuration of a monoscope as a component of the rigid endoscope according to the embodiment.

As illustrated in FIGS. 1, 2, and 4, the insertion portion 22 includes an outer lens barrel 28, a first monoscope 30, and a second monoscope 32.

As an example, the outer lens barrel 28 is made of a rigid material such as stainless steel and has a covered cylindrical shape having an outer diameter set to about 5.5 mm and extending in the first direction. A portion of the outer lens barrel 28 which is located on one side in the first direction is supported by a support tube portion 34, and a portion of the support tube portion 34 which is located on one side in the first direction is supported by the attachment portion 26. In each drawing, the first direction is indicated by an arrow X.

The first monoscope 30 includes a first inner lens barrel 36 and a first optical system 38. As an example, the first inner lens barrel 36 is made of a material having rigidity such as stainless steel, has an outer diameter set to about 2.5 mm, and has a cylindrical shape extending in the first direction. A light guide fiber 40 is provided on the outer periphery of the first inner lens barrel 36.

The light guide fiber 40 guides light emitted from a light source (not illustrated) to an end portion 36A (distal end portion) of the first inner lens barrel 36 which is located on the other side in the first direction and can emit illumination light from the end portion 36A. As illustrated in FIG. 6, the light guide fiber 40 extends to the light source through a guide pipe 42 provided in the support tube portion 34 and the inside of a guide tube 44 extending from the guide pipe 42. The first optical system 38 is disposed inside the first inner lens barrel 36.

The first optical system 38 includes an objective lens system 46 disposed on the end portion 36A side of the first inner lens barrel 36, an eyepiece system 48 disposed on the end portion 36B side opposite to the end portion 36A side of the first inner lens barrel 36, and a plurality of relay lenses 50 disposed between the objective lens system 46 and the eyepiece system 48.

In the objective lens system 46, objective lenses 52, 54, and 56 are arranged in series in the first direction to allow the formation of a first image 60 (see FIG. 3) of an observation target 58 (see FIG. 9) of the subject 20. The first image 60 formed by the objective lens system 46 is transmitted to the eyepiece system 48 through the plurality of relay lenses 50.

In the eyepiece system 48, eyepieces 62, 64, and 66 are arranged in series in the first direction to allow the formation of the first image 60 transmitted from the relay lens 50. The optical axis of the first optical system 38 configured as described above, that is, a first optical axis 68 extends in the first direction.

The second monoscope 32 includes a second inner lens barrel 70 and a second optical system 72. The second inner lens barrel 70 has the same configuration as the first inner lens barrel 36 and extends in parallel with the first inner lens barrel 36 in a state of being adjacent to the first inner lens barrel 36. The light guide fiber 40 is provided on the outer periphery of the second inner lens barrel 70, and the second optical system 72 is disposed inside the second inner lens barrel 70.

The second optical system 72 has the same configuration as the first optical system 38 and includes the objective lens system 46, the eyepiece system 48, and the plurality of relay lenses 50. The second optical system 72 can form a second image 74 (see FIG. 3) of the observation target 58. The optical axis of the second optical system 72, that is, a second optical axis 76, is parallel to the first optical axis 68 as the first inner lens barrel 36 and the second inner lens barrel 70 are positioned by an adjustment jig 78 as described later.

In the embodiment, as an example, the distance between the first optical axis 68 (the central axis of the first inner lens barrel 36) and the second optical axis 76 (the central axis of the second inner lens barrel 70) as viewed from the first direction is set to 3.2 mm. Hereinafter, a direction along a straight line passing through the first optical axis 68 and the second optical axis 76 as viewed from the first direction is referred to as a second direction, and a side opposite to the second optical system 72 with respect to the first optical system 38 is referred to as one side in the second direction. In each drawing, the second direction is indicated by an arrow Y.

In addition, the first optical system 38 and the second optical system 72 configured as described above can set the focal depth to be relatively deep and can form an image of the observation target 58 even if the eyepiece system 48 approaches or separates from the observation target 58 in a predetermined range. More specifically, in the embodiment, as an example, the viewing angles of the first optical system 38 and the second optical system 72 are set to 80° to 90°, and the focal lengths of the first optical system 38 and the second optical system 72 are set to 25 mm to 30 mm.

Figure 8:
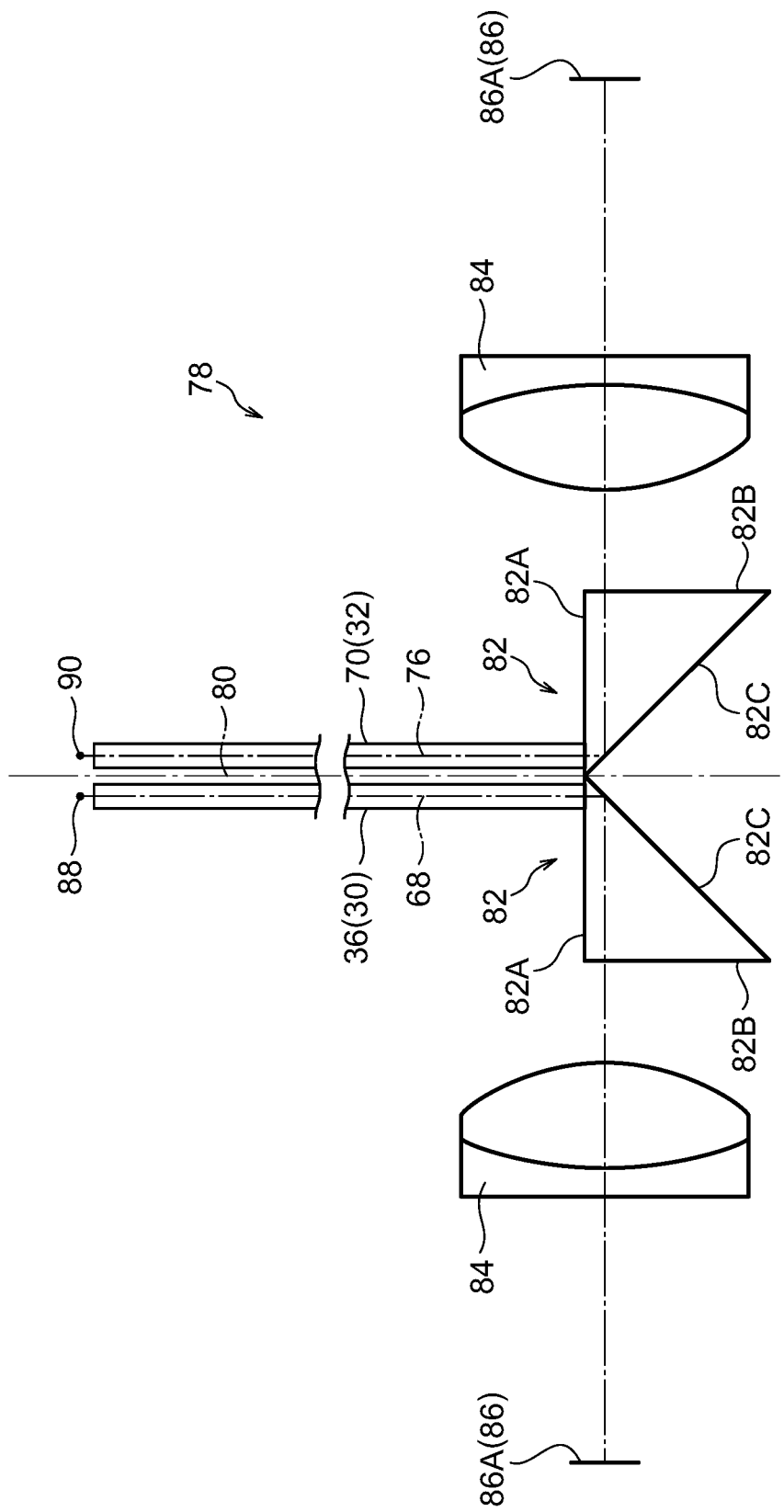
FIG. 8 is a schematic view schematically illustrating a state of the rigid endoscope at the time of adjustment according to the embodiment.

In this case, the adjustment jig 78 for adjusting the positional relationship between the first inner lens barrel 36 and the second inner lens barrel 70 will be described with reference to FIG. 8. The adjustment jig 78 includes a pair of prisms 82, a pair of lenses 84, and a pair of image sensing devices 86 arranged symmetrically with respect to a reference plane 80.

The prism 82 includes a planar portion 82A, a planar portion 82B orthogonal to the planar portion 82A, and a planar portion 82C connecting an end portion of the planar portion 82A and an end portion of the planar portion 82B. The prism 82 is disposed in a state where the planar portion 82A is orthogonal to the reference plane 80 and the planar portion 82B is separated from the reference plane 80.

The lens 84 is disposed on the opposite side of the reference plane 80 with respect to the prism 82 such that about a half of the lens overlaps the planar portion 82B when viewed from the thickness direction, and such that the optical axis is orthogonal to the planar portion 82B.

The image sensing device 86 is arranged on the opposite side of the reference plane 80 with respect to the lens 84 such that the central point of an imaging surface 86A is positioned on the optical axis of the lens 84, and can output an image formed on the imaging surface 86A as a picture on a monitor (not illustrated).

In addition, a first target 88 corresponding to one prism 82 and a second target 90 corresponding to the other prism 82 are arranged symmetrically with respect to the reference plane 80 at a position away from each planar portion 82A by a predetermined distance. Although the shapes of the first target 88 and the second target 90 can be arbitrarily set, these shapes are set to the same shape when viewed from the prism 82 side.

In the adjustment jig 78 configured as described above, the first inner lens barrel 36 is disposed such that the first optical axis 68 is orthogonal to the planar portion 82A with respect to the planar portion 82A of one prism 82, whereby the picture of the first target 88 captured by the image sensing device 86 corresponding to the prism 82 is displayed on one monitor.

The second inner lens barrel 70 is disposed with respect to the planar portion 82A of the other prism 82 such that the second optical axis 76 is orthogonal to the planar portion 82A, whereby the picture of the second target 90 captured by the image sensing device 86 corresponding to the prism 82 is displayed on the other monitor.

In the embodiment, the first inner lens barrel 36 and the second inner lens barrel 70 are positioned such that the picture of the first target 88 and the picture of the second target 90 are in focus and the center of the display surface of the monitor and the center of the picture coincide with each other. In this state, the first inner lens barrel 36 and the second inner lens barrel 70 are fixed to the outer lens barrel 28. The distance between the central axis of the first inner lens barrel 36 and the central axis of the second inner lens barrel 70 is maintained at 3.2 mm.

Referring back to FIG. 1, the imaging device 24 is a high-definition video camera compatible with full high vision or the like and includes a solid-state image sensing device 92 having a rectangular imaging surface 92A when viewed from the first direction and a housing portion 94 that stores the solid-state image sensing device 92.

Note that, as the solid-state image sensing device 92, a complementary metal oxide semiconductor (CMOS) image sensor or a charge coupled device (CCD) image sensor can be employed.

The housing portion 94 is coupled to the attachment portion 26, and the inside of the housing portion 94 communicates with the inside of the attachment portion 26.

Figure 3:
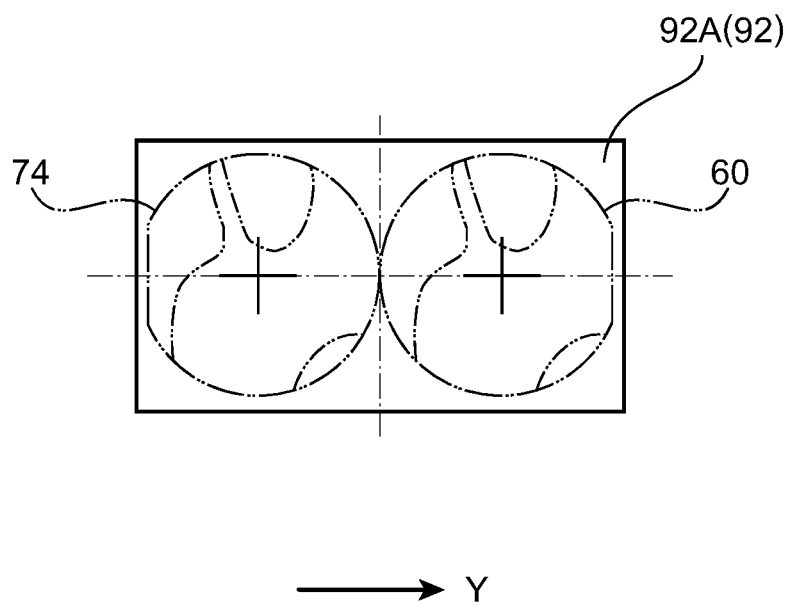
FIG. 3 is a front view schematically illustrating the configuration of a solid-state image sensing device provided in the rigid endoscope according to the embodiment.

Then, as illustrated in FIG. 3, on the imaging surface 92A, the first image 60 formed by a first light beam 96 (see FIG. 1) emerging from the observation target 58 and passing through the first optical system 38 and the attachment portion 26 and the second image 74 formed by a second light beam 98 (see FIG. 1) emerging from the observation target 58 and passing through the second optical system 72 and the attachment portion 26 are formed. Note that the solid-state image sensing device 92 is arranged such that the longitudinal direction of the imaging surface 92A is the second direction, and the first image 60 and the second image 74 are formed in parallel in the second direction.

The solid-state image sensing device 92 can convert light received by the imaging surface 92A into an electric signal. The electric signal is input to the picture display device 16 via a wiring portion 100 connected to the imaging device 24 as illustrated in FIG. 7.

Referring back to FIG. 1, the attachment portion 26 includes a cylindrical case portion 102. The case portion 102 includes a first lens prism 104, a first position adjustment lens 106 as a first position adjustment lens system, a first focus adjustment lens 108 as a first focus adjustment lens system, a second lens prism 110, a third lens prism 112, a second position adjustment lens 114 as a second position adjustment lens system, a second focus adjustment lens 116 and a fourth lens prism 118 as a second focus adjustment lens system, a first shielding portion 120, and a second shielding portion 122.

The first light beam 96 passing through the first optical system 38 can be adjusted by causing the first light beam 96 to pass through the first lens prism 104, the first position adjustment lens 106, the first focus adjustment lens 108, and the second lens prism 110.

More specifically, the first lens prism 104 is disposed on one side of the first optical system 38 in the first direction, and the first light beam 96 passes through the first lens prism 104 to be refracted to one side in the second direction and then to one side in the first direction. As a result, the distance between the optical path of the first light beam 96 and a center line CL of the insertion portion 22 becomes larger after the first light beam 96 passes through the first lens prism 104 than before the first light beam 96 passes through the first lens prism 104.

The first position adjustment lens 106 is disposed on one side of the first lens prism 104 in the first direction and can adjust the first light beam 96 such that the first light beam 96 having passed through the first lens prism 104 is focused at a predetermined position on the imaging surface 92A of the solid-state image sensing device 92. A plurality of first position adjustment lenses 106 may be arranged in series in the first direction.

The first focus adjustment lens 108 is disposed on one side of the first position adjustment lens 106 in the first direction such that the first light beam 96 having passed through the first position adjustment lens 106 passes through the first focus adjustment lens 108, and adjusts the focal position of the first optical system 38. The focal point of first optical system 38 herein means the focal point of the optical system through which the first light beam 96 including the first optical system 38 passes. Further, a plurality of first focus adjustment lenses 108 may be arranged in series in the first direction.

The second lens prism 110 is disposed on one side of the first focus adjustment lens 108 in the first direction, and the first light beam 96 passes through the second lens prism 110 to be refracted to the other side in the second direction and then to be refracted to one side in the first direction. As a result, the distance between the optical path of the first light beam 96 and the center line CL of the insertion portion 22 becomes smaller after the first light beam 96 passes through the second lens prism 110 than before the first light beam 96 passes through the second lens prism 110, and the first light beam 96 reaches the imaging surface 92A.

The second light beam 98 passing through the second optical system 72 can be adjusted by causing the second light beam 98 to pass through the third lens prism 112, the second position adjustment lens 114, the second focus adjustment lens 116, and the fourth lens prism 118.

More specifically, the third lens prism 112 is disposed on one side of the second optical system 72 in the first direction, and the second light beam 98 passes through the third lens prism 112 to be refracted to the other side in the second direction and then to one side in the first direction. As a result, the distance between the optical path of the second light beam 98 and the center line CL of the insertion portion 22 becomes larger after the second light beam 98 passes through the third lens prism 112 than before the second light beam 98 passes through the third lens prism 112.

The second position adjustment lens 114 is disposed on one side of the third lens prism 112 in the first direction and can adjust the second light beam 98 such that the second light beam 98 having passed through the third lens prism 112 is focused at a predetermined position on the imaging surface 92A of the solid-state image sensing device 92. A plurality of second position adjustment lenses 114 may be sequentially arranged in the first direction.

The second focus adjustment lens 116 is disposed on one side of the second position adjustment lens 114 in the first direction such that the second light beam 98 having passed through the second position adjustment lens 114 passes through the second focus adjustment lens 116, and adjusts the focal position of the second optical system 72. The focal point of the second optical system 72 herein means the focal point of the optical system through which the second light beam 98 including the second optical system 72 passes. Further, a plurality of second focus adjustment lenses 116 may be arranged in series in the first direction.

The fourth lens prism 118 is disposed on one side of the second focus adjustment lens 116 in the first direction, and the second light beam 98 passes through the fourth lens prism 118 to be refracted to one side in the second direction and then to be refracted to one side in the first direction. As a result, the distance between the optical path of the second light beam 98 and the center line CL of the insertion portion 22 becomes smaller after the second light beam 98 passes through the fourth lens prism 118 than before the second light beam 98 passes through the fourth lens prism 118, and the second light beam 98 reaches the imaging surface 92A.

In the embodiment, the first lens prism 104, the first position adjustment lens 106, the first focus adjustment lens 108, the second lens prism 110, the third lens prism 112, the second position adjustment lens 114, the second focus adjustment lens 116, and the fourth lens prism 118 are arranged as described above. With this arrangement, the first image 60 and the second image 74 are formed on the imaging surface 92A of the solid-state image sensing device 92 such that the first image 60 and the second image 74 do not overlap each other and the central point (reference point) of the first image 60 and the central point (reference point) of the second image 74 coincide with each other in the transverse direction (height direction) of the imaging surface 92A. Note the following.

The first shielding portion 120 has the plate thickness direction as the first direction and a rectangular plate shape when viewed from the first direction and extends from a portion of the peripheral wall portion 102A of the case portion 102 which is located one side in the second direction to the other side in the second direction. The first shielding portion 120 is disposed at the same position as the focal point of the optical system including the first optical system 38, the first lens prism 104, and the first position adjustment lens 106 in the first direction and covers a part of the first position adjustment lens 106 which is located on one side in the second direction when viewed from the first direction.

The first shielding portion 120 shields a part of the first light beam 96 so that a portion included in the first image 60 (in a state where the first shielding portion 120 is not provided) and not included in the second image 74 does not appear on the imaging surface 92A.

The second shielding portion 122 has the plate thickness direction as the first direction and a rectangular plate shape when viewed from the first direction and extends from a portion of the peripheral wall portion 102A of the case portion 102 which is located the other side in the second direction to one side in the second direction. The second shielding portion 122 is disposed at the same position as the focal point of the optical system including the second optical system 72, the third lens prism 112, and the second position adjustment lens 114 in the first direction and covers a part of the second position adjustment lens 114 which is located on the other side in the second direction when viewed from the first direction.

The second shielding portion 122 shields a part of the second light beam 98 so that a portion included in the second image 74 (in a state where the second shielding portion 122 is not provided) and not included in the first image 60 does not appear on the imaging surface 92A.

Note that the rigid endoscope 12 can adjust the relative positional relationship with the subject 20 in a predetermined range by adjusting the first support arm 14. In the embodiment, the rigid endoscope 12 can be moved in the extending direction of the first optical axis 68 and the second optical axis 76 with respect to the subject 20, that is, in the first direction by adjustment of the first support arm 14 and relative movement of the rigid endoscope 12 with respect to the first support arm 14.

Figure 5:
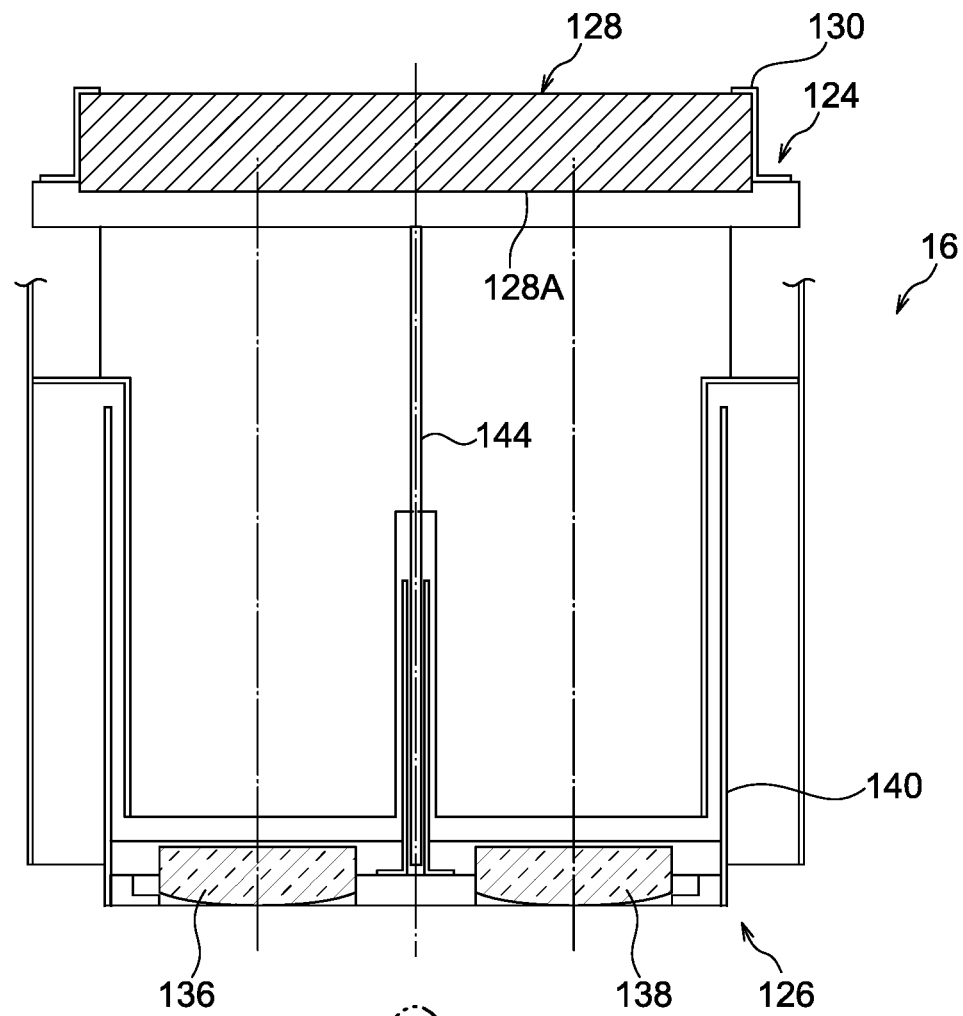
FIG. 5 is a cross-sectional view schematically illustrating the configuration of a picture display device provided in the rigid scope device according to the embodiment.
Figure 10:
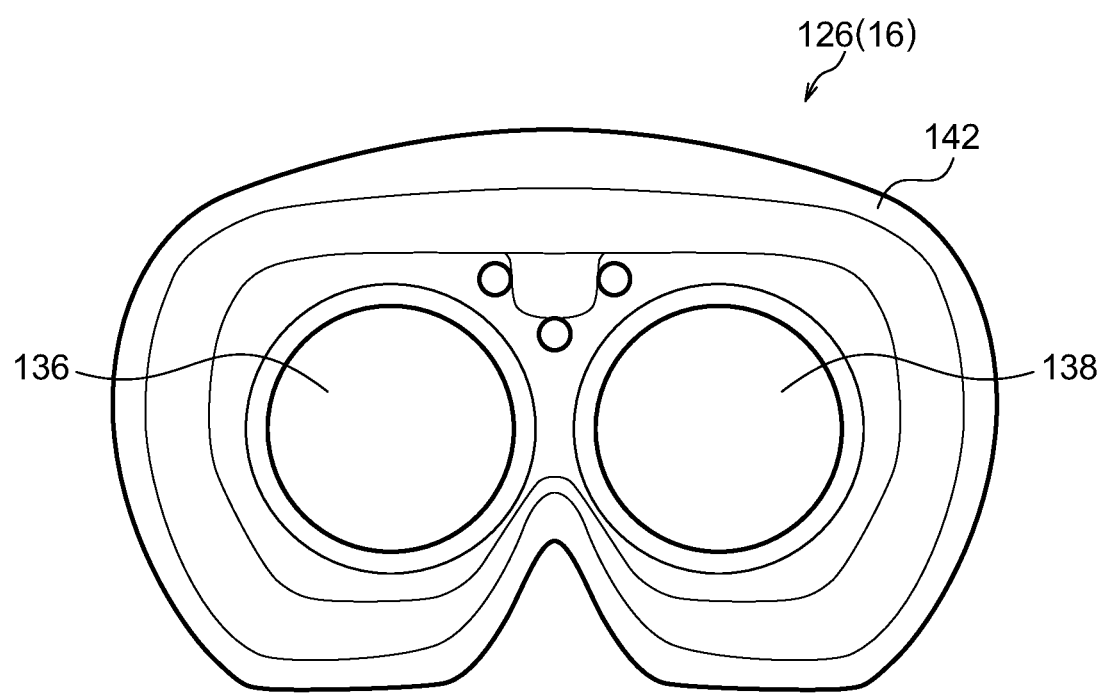
FIG. 10 is a front view schematically illustrating the configuration of the picture display device provided in the rigid scope device according to the embodiment.

On the other hand, as illustrated in FIGS. 5, 7, and 10, the picture display device 16 includes a device main body 124 and a picture visibility assist unit 126.

The device main body 124 includes a picture display unit 128 and a housing 130 that houses the picture display unit 128. The picture display unit 128 includes a high-definition monitor compatible with full high vision or the like and a display surface 128A having a rectangular shape in a front view.

Figure 11:
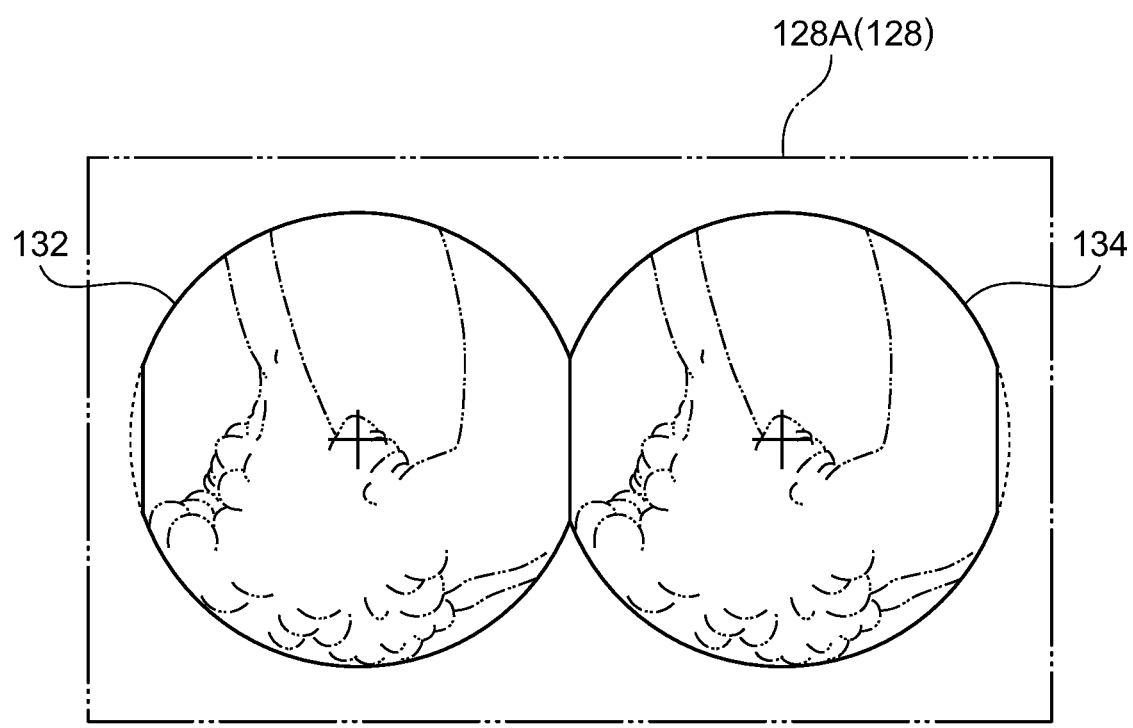
FIG. 11 is a diagram schematically illustrating a state of an observation target viewed from the picture display device provided in the rigid scope device according to the embodiment.

As described above, the first image 60 and the second image 74 are input as electric signals from the solid-state image sensing device 92 to the picture display unit 128, and a picture is output on the basis of the electric signals. As illustrated in FIG. 11, on display surface 128A, a first picture 132 corresponding to the first image 60 is displayed on the left side of the display surface 128A in the longitudinal direction (one side in the longitudinal direction). In addition, a second picture 134 corresponding to the second image 74 is displayed on the right side of the display surface 128A in the longitudinal direction (the other side in the longitudinal direction).

In the embodiment, as described above, the first light beam 96 and the second light beam 98 are adjusted by the attachment portion 26 so as to display the first picture 132 and the second picture 134 on the display surface 128A such that the first picture 132 and the second picture 134 do not overlap each other and the central point (reference point) of the first picture 132 and the central point (reference point) of the second picture 134 coincide with each other in the transverse direction (height direction) of the display surface 128A as viewed from an observer 146. Referring to FIG. 11, the height direction of the display surface 128A is indicated by an arrow Z.

Note that the distance between the central point of the first picture 132 and the central point of the second picture 134 is preferably set to the standard interpupillary distance of adults. In the embodiment, as an example, the distance between the central point of the first picture 132 and the central point of the second picture 134 is set to 65 mm.

On the other hand, the picture visibility assist unit 126 includes a first magnifying lens 136 for the left eye, a second magnifying lens 138 for the right eye, and a case portion 140 to which the first magnifying lens 136 and the second magnifying lens 138 are attached.

The case portion 140 is attached to the device main body 124 so as to be movable relative to the device main body 124 in the thickness direction of first magnifying lens 136 and the second magnifying lens 138 (the direction orthogonal to the display surface 128A). The case portion 140 is provided with an eye cap portion 142 surrounding the first magnifying lens 136 and the second magnifying lens 138 from the periphery. In addition, the case portion 140 is provided with a separating plate portion 144 as a picture separation unit disposed between the first magnifying lens 136 and the second magnifying lens 138 when viewed from the thickness direction of the first magnifying lens 136 and the second magnifying lens 138, and the inside of the case portion 140 is partitioned by the separating plate portion 144.

When the observer 146 looks into the display surface 128A of the picture display unit 128 from the eye cap portion 142 through the first magnifying lens 136 and the second magnifying lens 138, as illustrated in FIG. 11, the separating plate portion 144 can hide the second picture 134 when viewed from the first magnifying lens 136 and can hide the first picture 132 when viewed from the second magnifying lens 138.

Referring to FIG. 11, a portion of the first picture 132 which is surrounded by the dotted line on the left side in the longitudinal direction of the display surface 128A is a portion corresponding to a portion included in the first image 60 and not included in the second image 74 in the first picture 132 in a state where the above first shielding portion 120 is not provided.

A portion of the second picture 134 which is surrounded by the dotted line on the right side in the longitudinal direction of the display surface 128A is a portion corresponding to a portion included in the second image 74 and not included in the first image 60 in the second picture 134 in a state where the above second shielding portion 122 is not provided.

Note that the position of the picture display device 16 can be adjusted in a predetermined range by adjusting the second support arm 18.

Functions and Effects of Present Embodiment

The functions and effects of the present embodiment will be described next.

In the embodiment, as illustrated in FIGS. 1 and 2, the insertion portion 22 of the rigid endoscope 12 includes the outer lens barrel 28 made of a rigid material and extending in the first direction, and the first inner lens barrel 36 and the second inner lens barrel 70 are disposed in the outer lens barrel 28. Each of the first inner lens barrel 36 and the second inner lens barrel 70 is made of a rigid material. The first inner lens barrel 36 extends in the first direction. The second inner lens barrel 70 is disposed adjacent to the first inner lens barrel 36 and extends in parallel with the first inner lens barrel 36.

The first optical system 38 including the first optical axis 68 extending in the first direction is disposed inside the first inner lens barrel 36, and the second optical system 72 including the second optical axis 76 extending in parallel with the first optical axis 68 is disposed inside the second inner lens barrel 70. The solid-state image sensing device 92 is disposed on one side of the first optical system 38 and the second optical system 72 in the first direction.

Figure 9:
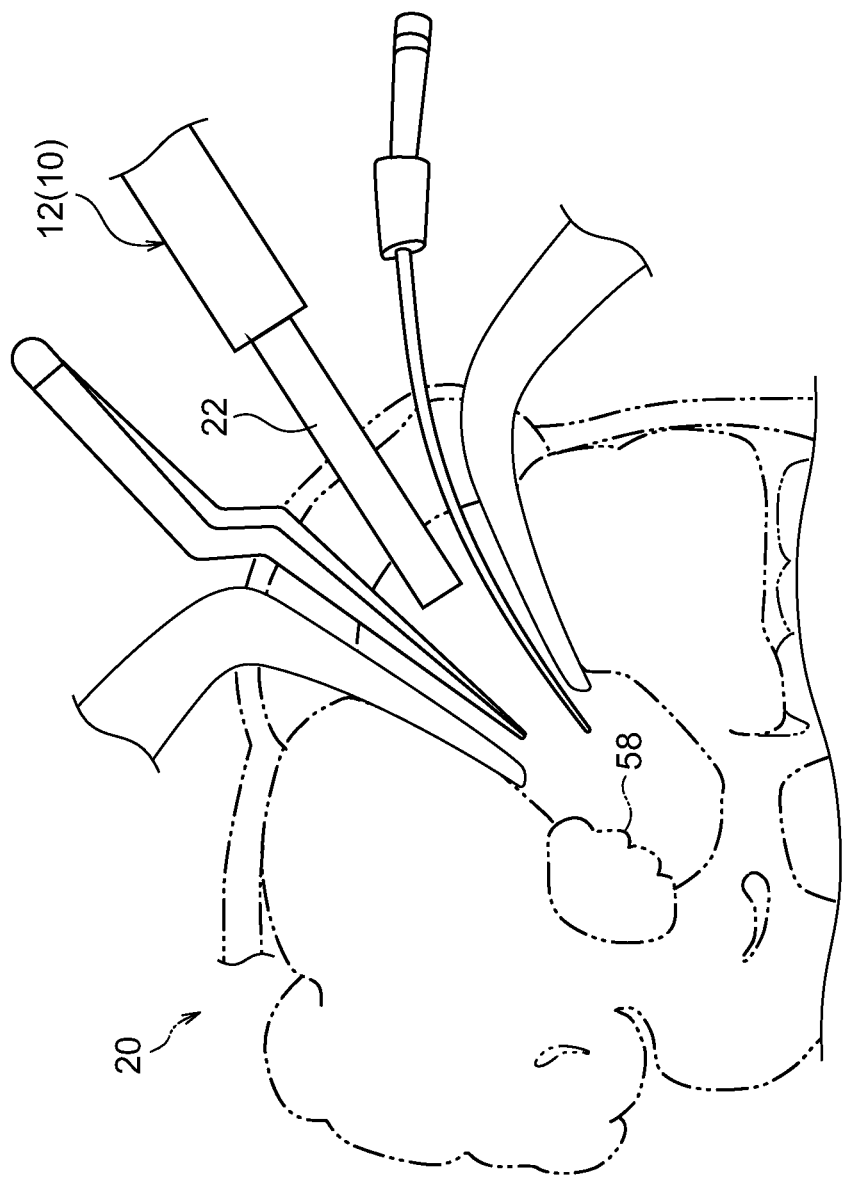
FIG. 9 is a schematic view schematically illustrating a state of the rigid scope device at the time of use according to the embodiment.

As illustrated in FIG. 9, at the time of observing the observation target 58 of the subject 20, the insertion portion 22 is inserted into the subject 20 from the opening of the subject 20, and the distal end portion of the insertion portion 22 is directed to the observation target 58. Accordingly, the observation target 58 can be stereoscopically viewed using the images formed on the imaging surface 92A of the solid-state image sensing device 92 by the first optical system 38 and the second optical system 72.

Meanwhile, in a configuration in which the solid-state image sensing device 92 is provided for each of the first optical system 38 and the second optical system 72, a stereoscopic picture of the observation target 58 is generated by processing signals based on images formed on different imaging surfaces 92A. Therefore, depending on the signal processing, the stereoscopic picture of the observation target 58 obtained based on these images may deviate from the actual state of the observation target 58.

In this case, in the embodiment, as illustrated in FIG. 3, the single solid-state image sensing device 92 is disposed for the first optical system 38 and the second optical system 72. The first image 60 formed by the first light beam 96 emerging from the observation target 58 and passing through the first optical system 38 and the second image 74 formed by the second light beam 98 emerging from the observation target 58 and passing through the second optical system 72 are formed on the imaging surface 92A of the solid-state image sensing device 92. The solid-state image sensing device 92 then converts the first image 60 and the second image 74 into electric signals.

On the other hand, in the picture display unit 128, as illustrated in FIG. 11, the first picture 132 corresponding to the first image 60 and the second picture 134 corresponding to the second image 74 are displayed on the display surface 128A based on the electric signal obtained by the solid-state image sensing device 92. Accordingly, in the embodiment, when the observer 146 views the display surface 128A of the picture display unit 128, the observer can perform stereoscopic viewing of the observation target 58 by the parallel method by using the first image 60 and the second image 74 obtained by performing signal processing on the first picture 132 and the second picture 134 in a similar manner.

In the embodiment, as illustrated in FIG. 1, the attachment portion 26 is interposed between the outer lens barrel 28 and the solid-state image sensing device 92. The attachment portion 26 adjusts the first light beam 96 that has passed through the first optical system 38 and the second light beam 98 that has passed through the second optical system 72. As a result, on the display surface 128A of the picture display unit 128, the first picture 132 and the second picture 134 are displayed so that the reference point of the observation target 58 in the first picture 132 and the reference point in the second picture 134 have the same height as viewed from the observer 146 without overlapping each other.

More specifically, the attachment portion 26 includes the first lens prism 104 through which the first light beam 96 passes, the first position adjustment lens 106, the first focus adjustment lens 108, and the second lens prism 110. The attachment portion 26 includes the third lens prism 112 through which the second light beam 98 passes, the second position adjustment lens 114, the second focus adjustment lens 116, and the fourth lens prism 118.

The first lens prism 104 is disposed on one side of the first optical system 38 in the first direction, and the first light beam 96 passing through the first optical system 38 is refracted by the first lens prism 104 and travels to the first position adjustment lens 106. The first light beam 96 is adjusted by the first position adjustment lens 106 such that the first image 60 is formed at a predetermined position on the imaging surface 92A.

The first light beam 96 having passed through the first position adjustment lens 106 travels to the first focus adjustment lens 108 disposed on one side of the first position adjustment lens 106 which is located in the first direction. The focal position of the first optical system 38 is adjusted such that the first light beam 96 converges at a predetermined point through the first focus adjustment lens 108. The first light beam 96 that has passed through the first focus adjustment lens 108 travels to the imaging surface 92A through the second lens prism.

The third lens prism 112 is disposed on one side of the second optical system 72 in the first direction, and the second light beam 98 passing through the second optical system 72 is refracted by the third lens prism 112 and travels to the second position adjustment lens 114. The second light beam 98 is adjusted by the second position adjustment lens 114 such that the second image 74 is formed at a predetermined position on the imaging surface 92A.

The second light beam 98 having passed through the second position adjustment lens 114 travels to the second focus adjustment lens 116 disposed on one side of the second position adjustment lens 114 which is located in the first direction. The focal position of the second optical system 72 is adjusted such that the second light beam 98 converges at a predetermined point through the second focus adjustment lens 116. The second light beam 98 that has passed through the second focus adjustment lens 116 travels to the imaging surface 92A through the fourth lens prism 118.

In the configuration in which the first light beam 96 linearly advances from the first optical system 38 toward the first position adjustment lens 106 along the first direction, it is conceivable that a space for arranging the first position adjustment lens 106 and the first focus adjustment lens 108 cannot be secured. On the other hand, in the configuration in which the first light beam linearly advances from the first focus adjustment lens 108 toward the solid-state image sensing device 92 along the first direction, it is conceivable that the degree of freedom of the shape and size of the solid-state image sensing device 92 is reduced.

In the configuration in which the second light beam 98 linearly advances from the second optical system 72 toward the second position adjustment lens 114 along the first direction, it is conceivable that a space for arranging the second position adjustment lens 114 and the second focus adjustment lens 116 cannot be secured. On the other hand, in the configuration in which the second light beam 98 linearly advances from the second focus adjustment lens 116 toward the solid-state image sensing device 92 along the first direction, it is conceivable that the degree of freedom of the shape and size of the solid-state image sensing device 92 is reduced.

In this case, in the embodiment, the first lens prism 104 refracts the first light beam 96 to one side in the second direction. On the other hand, the second lens prism 110 refracts the first light beam 96 toward the other side in the second direction.

The third lens prism 112 refracts the second light beam 98 toward the other side in the second direction. On the other hand, the fourth lens prism 118 refracts the second light beam 98 toward one side in the second direction.

Therefore, in the embodiment, by refracting the first light beam 96 by the first lens prism 104 and refracting the second light beam by the second lens prism 110, it is possible to secure a space for arranging the first position adjustment lens 106, the first focus adjustment lens 108, the second position adjustment lens 114, and the second focus adjustment lens 116. Furthermore, by refracting the first light beam 96 by the second lens prism 110 and refracting the second light beam 98 by the fourth lens prism 118, the distance between the optical paths of the first light beam 96 and the second light beam 98 can be adjusted in accordance with the shape and size of the solid-state image sensing device 92.

In the embodiment, the attachment portion 26 includes the first shielding portion 120 and the second shielding portion 122. The first shielding portion 120 is disposed on one side in the second direction between the first position adjustment lens 106 and the first focus adjustment lens 108, and the first light beam 96 is shielded by the first shielding portion 120 such that a picture corresponding to a portion included in the first image 60 and not included in the second image 74 is not included in the first picture 132.

On the other hand, the second shielding portion 122 is disposed on the other side in the second direction between the second position adjustment lens 114 and the second focus adjustment lens 116, and the second light beam 98 is shielded by the second shielding portion 122 such that a picture corresponding to a portion included in the second image 74 and not included in the first image 60 is not included in the second picture 134. Accordingly, in the embodiment, since the same part of the observation target 58 can be displayed in the first picture 132 and the second picture 134 displayed on the display surface 128A of the picture display unit 128, the observer 146 can observe the observation target 58 by stereoscopic vision with high accuracy.

Further, in the embodiment, the picture visibility assist unit 126 movable in a direction orthogonal to the display surface 128A of the picture display unit 128 is provided. The picture visibility assist unit 126 includes the first magnifying lens 136 for the left eye and the second magnifying lens 138 for the right eye. By moving the picture visibility assist unit 126 in the direction orthogonal to the display surface, the first picture 132 can be enlarged by the first magnifying lens 136, and the second picture 134 can be enlarged by the second magnifying lens 138. Therefore, the observer 146 can observe the observation target 58 in more detail.

Moreover, by moving the picture visibility assist unit 126 in the direction orthogonal to the display surface, the apparent distance between the first picture 132 and the second picture 134 viewed by the observer 146 can be adjusted to a distance corresponding to the distance between the pupils of the observer 146. As a result, the observer 146 can smoothly perform stereoscopic viewing of the observation target 58.

In addition, in the embodiment, the picture visibility assist unit 126 includes the separating plate portion 144, and when the observer 146 looks at the display surface 128A of the picture display unit 128 with the right eye from the first magnifying lens 136, the first picture 132 is visible, but the second picture 134 is hidden by the separating plate portion 144. When the observer 146 looks at the display surface 128A of the picture display unit 128 with the left eye from the second magnifying lens 138, the second picture 134 is visible, but the first picture 132 is hidden by the separating plate portion 144. Therefore, in the embodiment, the observer 146 can observe the observation target 58 by more accurate stereoscopic vision.

As described above, according to the rigid scope device 10 according to the embodiment, it is possible to observe the observation target 58 in a state closer to an actual state.

Figure 12:
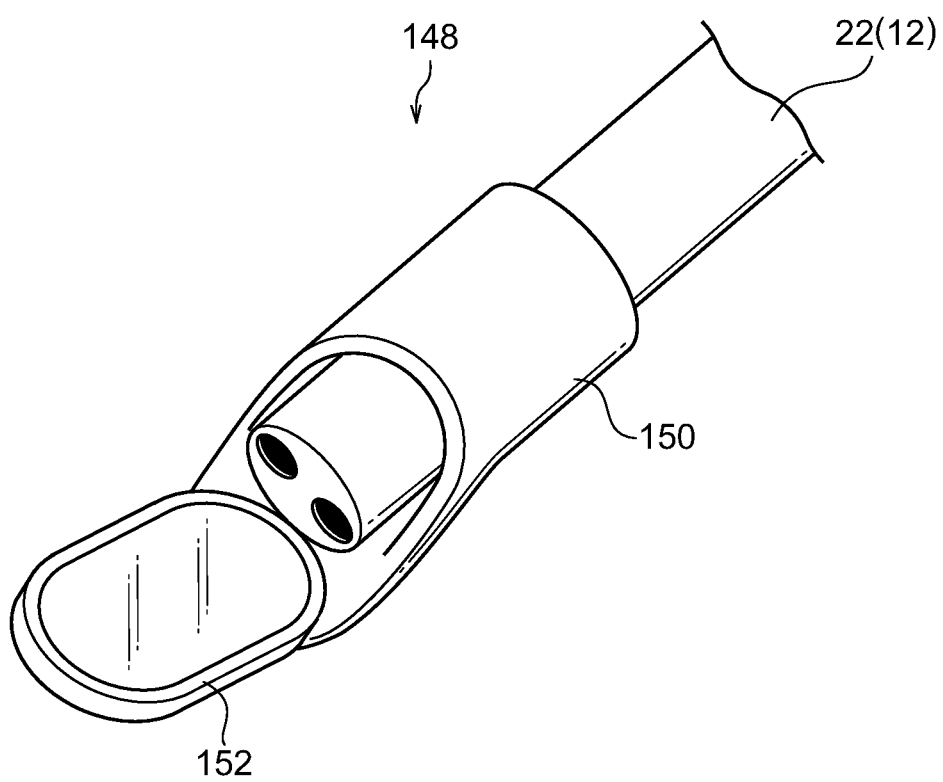
FIG. 12 is a perspective view schematically illustrating the configuration of a reflector unit attached to the rigid endoscope according to the embodiment.

Furthermore, in present embodiment, as illustrated in FIG. 12, the reflecting mirror unit 148 may be attached to the distal end portion of the insertion portion 22. The reflecting mirror unit 148 includes an attachment cylindrical portion 150 attached to the distal end portion of the insertion portion 22 and a reflecting mirror 152 pivotally supported by the attachment cylindrical portion 150. According to such a configuration, even when the observation target 58 is located at a position where it is difficult to directly observe with the rigid endoscope 12, the observation target 58 can be observed by stereoscopic vision.

Note that, in the embodiment, the first light beam 96 and the second light beam 98 can be adjusted by the attachment portion 26, but the first light beam 96 or the second light beam 98 may be adjusted by the attachment portion 26 according to, for example, the use of the rigid scope device 10.

Furthermore, in the embodiment, the rigid scope device 10 includes the rigid endoscope 12, but the present invention is not limited thereto. That is, the rigid scope device 10 may include a laparoscope in which the outer diameter of the insertion portion 22 of the rigid endoscope 12 is changed to about 10 mm. According to such a configuration, the state in the abdominal cavity of the subject 20 can be observed by stereoscopic vision. Furthermore, the rigid scope device 10 may include a rigid exoscope in which the length of the insertion portion 22 of the rigid endoscope 12 is set to be short and the outer diameter of the insertion portion 22 is set to be large. According to such a configuration, the observation target 58 can be observed by stereoscopic vision over a wide range from the outside of the subject 20.

The invention claimed is:

1. A rigid scope device, comprising:
an outer lens barrel made of a rigid material and extending in a first direction;
a first inner lens barrel made of a rigid material, disposed in the outer lens barrel, and extending in the first direction;
a first optical system disposed in the first inner lens barrel and including a first optical axis extending in the first direction;
a second inner lens barrel made of a rigid material, disposed adjacent to the first inner lens barrel in the outer lens barrel, and extending in parallel with the first inner lens barrel;
a second optical system disposed in the second inner lens barrel and including a second optical axis extending in parallel with the first optical axis;
a single solid-state image sensing device that is disposed on one side of the first optical system and the second optical system in the first direction, that includes an imaging surface on which a first image is formed by a first light beam emerging from an observation target and passing through the first optical system, and a second image is formed by a second light beam emerging from the observation target and passing through the second optical system, and that is configured to convert light received by the imaging surface into an electric signal;
a picture display unit including a display surface configured to display a first picture corresponding to the first image and a second picture corresponding to the second image based on the electric signal; and
an optical path adjustment unit interposed between the outer lens barrel and the solid-state image sensing device,
the optical path adjustment unit being configured to adjust at least one of the first light beam or the second light beam on the display surface, such that the first picture and the second picture do not overlap each other and a reference point of the observation target in the first picture and the reference point in the second picture are located at a same height as viewed by an observer,
wherein the optical path adjustment unit is configured to adjust the first light beam and the second light beam and includes:
a first lens prism disposed on one side of the first optical system in the first direction and configured to refract the first light beam to one side in a second direction at an opposite side of the first optical system from the second optical system, the second direction being a direction along a straight line passing through the first optical axis and the second optical axis as viewed from the first direction,
a first position adjustment lens system that adjusts the first light beam refracted by the first lens prism such that the first image is formed at a predetermined position,
a first focus adjustment lens system that is disposed on one side of the first position adjustment lens system in the first direction and adjusts a focal position of the first optical system,
a second lens prism configured to refract the first light beam passing through the first focus adjustment lens system to the other side in the second direction,
a third lens prism disposed on one side of the second optical system in the first
direction and configured to refract the second light beam toward the other side in the second direction,
a second position adjustment lens system that adjusts the second light beam refracted by the third lens prism such that the second image is formed at a predetermined position,
a second focus adjustment lens system that is disposed on one side of the second position adjustment lens system in the first direction and adjusts a focal position of the second optical system,
a fourth lens prism configured to refract the second light beam passing through the second focus adjustment lens system to the one side in the second direction,
a first shielding portion that is disposed on the one side in the second direction between the first position adjustment lens system and the first focus adjustment lens system and shields the first light beam such that a picture corresponding to a portion included in the first image and not included in the second image is not included in the first picture, and
a second shielding portion that is disposed on the other side in the second direction between the second position adjustment lens system and the second focus adjustment lens system and shields the second light beam such that a picture corresponding to a portion included in the second image and not included in the first image is not included in the second picture,
wherein the first shielding portion has a plate thickness direction as the first direction and a rectangular plate shape when viewed from the first direction and extends from a portion of a peripheral wall portion of a case portion which is located one side in the second direction to the other side in the second direction, and
wherein the second shielding portion has a plate thickness direction as the first direction and a rectangular plate shape when viewed from the first direction and extends from a portion of the peripheral wall portion of the case portion which is located the other side in the second direction to the one side in the second direction.

2. The rigid scope device according to claim 1, further comprising a picture visibility assist unit that is movable in a direction orthogonal to the display surface and includes a first magnifying lens for a left eye configured to enlarge the first picture and a second magnifying lens for a right eye configured to enlarge the second picture.

3. The rigid scope device according to claim 2, wherein the picture visibility assist unit further includes a picture separation unit configured to hide the second picture when viewed from the first magnifying lens and hide the first picture when viewed from the second magnifying lens.

* * * * *